United States Patent

Bugaut et al.

[11] 4,094,635
[45] June 13, 1978

[54] META-AMINOPHENOL SULFONAMIDES AS COUPLERS IN HAIR DYE COMPOSITIONS

[75] Inventors: Andrée Bugaut, Boulogne; Chantal S. Fourcadier, Paris, both of France

[73] Assignee: L'Oreal, Paris, France

[21] Appl. No.: 722,610

[22] Filed: Sep. 13, 1976

[30] Foreign Application Priority Data

Sep. 9, 1976    France ............................... 76 27125

[51] Int. Cl.² ....................... A61K 7/12; C07C 143/72
[52] U.S. Cl. ............................................. 8/11; 8/10.1; 8/10.2; 260/556 A; 260/556 R
[58] Field of Search ........................... 8/11, 10.1, 10.2; 260/556 A

[56] References Cited

U.S. PATENT DOCUMENTS 3,743,678  7/1973  Halasz ..................................... 8/10.2

OTHER PUBLICATIONS

Rattee, I. D. and Breuer, M. M., "The Physical Chemistry of Dye Adsorption" (Academic Press, 1974), pp. 295-297.
Corbett, J. F., "Hair Dyes" in Venkataramans, The Chemistry of Synthetic Dyes, vol. V (Academic Press, 1971), pp. 475-534.

*Primary Examiner*—A. Lionel Clingman
*Attorney, Agent, or Firm*—Brisebois & Kruger

[57] ABSTRACT

Couplers responding to the formula

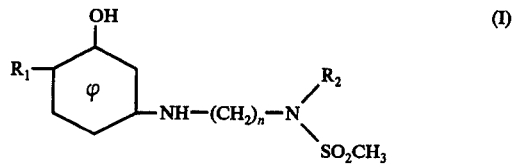

in which formula $R_1$ represents an alkyl radical having 1 to 4 carbon atoms, $R_2$ represents a hydrogen atom or an alkyl radical having 1 to 4 carbon atoms, and n is a number having for value 2 or 3.

These couplers are particularly adapted for use in dyeing compositions containing paraphenylenediamines responding to the general formula

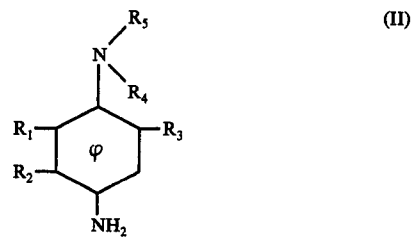

or salts of the corresponding acids; formula in which $R_1$, $R_2$ and $R_3$ are identical or different and represent a hydrogen atom, an alkyl radical having 1 to 2 carbon atoms or an alkoxy radical having 1 to 2 carbon atoms, $R_4$ and $R_5$ are identical or different and represent a hydrogen atom, an alkyl radical, hydroxyalkyl, alkoxyalkyl in which the alkoxy group comprises 1 to 2 carbon atoms, carbamylalkyl, mesylaminoalkyl, acetylaminoalkyl, ureidoaminoalkyl, carbethoxyaminoalkyl, the alkyl groups in $R_4$ and $R_5$ having 1 to 3 atoms of carbon, with the reservation that $R_1$ or $R_3$ represent hydrogen while $R_4$ and $R_5$ do not represent a hydrogen atom.

11 Claims, No Drawings

META-AMINOPHENOL SULFONAMIDES AS COUPLERS IN HAIR DYE COMPOSITIONS

In the field of dyeing keratinic fibers and more particularly human hair, the dominant process consists in simultaneously applying to the fiber in an alkaline oxidizing medium representatives judiciously chosen from two very distinct classes of chemical compositions: on the one hand, the paraphenylenediamines and the paraaminophenols called oxidation bases, on the other hand, the metaphenylenediamines, the metaaminophenols or the metadiphenols called couplers. The association of an oxidation base and a coupler leads, in an alkaline oxidizing medium, to the formation of a colored compound: indamine, indoaniline or indophenol depending on the nature of the compounds present.

In order to be selected, the oxidation bases and the couplers must both have the advantage of a good innocuousness and impart to the keratinic fibers shades of good quality, in particular stable to light, to inclement weather, and to shampooing.

The present invention has for purpose to propose a new family of couplers having the advantage of a good inocuousness and capable of giving valuable results when they are used in combination with oxidation bases for dyeing keratinic fibers.

The present invention has for object, as a new industrial product, a new chemical compound having the general formula

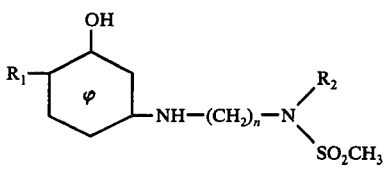

(I)

in which formula $R_1$ represents an alkyl radical having 1 to 4 carbon atoms, $R_2$ represents a hydrogen atom or an alkyl radical having 1 to 4 carbon atoms, and $n$ is a number having for value 2 or 3.

The new chemical compounds according to the invention may be easily prepared by using as starting material a 2-alkyl 5-amino phenol, and causing an N-halogenoalkyl-amine to react on the starting material and by mesylating the resulting product by the action of methane-sulfochloride.

Taking into account the possibilities of economically supplying N-halogenoalkyl-amine and the possibilities of easy preparation by the use of this reactant, the invention has been limited to the case in which the parameter N has the value 2 or 3.

The new chemical compounds of formula (I) are particularly usable as couplers for dyeing compositions for keratinic fibers. The present invention thus also has for object a dyeing composition for keratinic fibers and, more particularly, for human hair, containing, in aqueous solution, at least one oxidation base, characterized by the fact that it contains, as a coupler, at least one compound of formula (I).

When the couplers of formula (I) are associated, in an alkaline oxidizing medium, with most paraphenylenediamines and paraaminophenols, they impart to the keratinic fibers shades having a good stability to light, to inclement weather, and to shampooing. Shades vary according to the oxidation base used: they run from orange shades when the oxidation base is a paraaminophenol, to red, purplish red and more or less violet or greenish blue shades when the oxidation base is a paraphenylenediamine of the type hereinafter defined. It has been found, moreover, that the couplers of formula (I) have, in tinctorial compositions, in an alkaline ammoniacal medium, good preservation during storage.

In the dyeing compositions according to the invention, one may advantageously use as oxidation base paraphenyenediamines of the general formula:

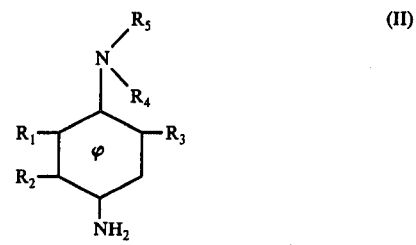

(II)

or corresponding acid salts; formula in which $R_1$, $R_2$ and $R_3$ are identical or different and represent a hydrogen atom, an alkyl radical having 1 to 2 carbon atoms or an alkoxy radical having 1 to 2 carbon atoms, $R_4$ and $R_5$ are identical or different and represent a hydrogen atom, an alkyl radical, hydroxyalkyl, alkoxyalkyl in which the alkoxy group comprises 1 to 2 carbon atoms, carbamylalkyl mesylaminoalkyl, acetylaminoalkyl, ureidoaminoalkyl, carbethoxyaminoalkyl, the alkyl groups in $R_4$ and $R_5$ having 1 to 3 atoms of carbon, with the reservation that $R_1$ or $R_3$ represent hydrogen while $R_4$ and $R_5$ do not represent a hydrogen atom. Among the paraphenylenediamines of formula (II), it is necessary to particularly mention paraphenylenediamine, 2,6-dimethyl paraphenylenediamine, 2,6-dimethyl-5-methoxy paraphenylenediamine, 4-amino-N-methyl aniline, 4-amino-N-methoxyethyl aniline, 4-amino-N,N-di-$\beta$-hydroxyethyl aniline, 4-amino-N-ethyl-N-carbamylmethyl aniline, 4-amino-N-ethyl-N-mesylaminoethyl aniline.

In the dyeing compositions according to the invention one may also advantageously use as oxidation base the paraaminophenols such, for example, as paraaminophenol, 2-methyl-4-amino phenol, 3-chloro-4-amino phenol.

In a surprising manner it has been found that the couplers of formula (I) give, with the greater part of the paraphenylenediamines of formula (II) or with the above mentioned paraaminophenols shades having good stability to light and having good stability to storage in an ammoniacal medium, whereas on the contrary, analogous compounds having the same general formula (I), but in which $R_1$ is an alkoxy radical or a halogen, do not have these properties and cannot, in consequence, constitute satisfactory couplers.

The dyeing compositions according to the invention may contain, moreover, in addition to the coupler or couplers of formula (I) for the oxidation base or bases associated therewith, the following couplers taken singly or in combination:

(a) metaphenylenediamines such as 2,4-diamino anisole, 2,4-diamino phenoxyethanol, (2-amino-4-amino-N-methyl) phenoxyethanol, (2,4-diamino) phenyl-$\beta$-methoxyethylether, 2-carbamylmethylamino-4-amino anisole;

(b) other metaaminophenols such as metaaminophenol, 2-methyl-5-amino phenol, 2-methyl-5-amino-N-

β-hydroxyethyl phenol, 2-methyl-5-carbamylmethylamino phenol, 2,6-dimethyl-5-amino phenol;

(c) metaacetylaminophenols such as 2-methyl-5-acetylamino phenol, 2,6-dimethyl-5-acetylamino phenol, 2-methoxy-5-acetylamino phenol;

(d) the metaureidophenols such as 2-methyl-5-ureido phenol;

(e) the metacarbethoxyphenols such as 2-methyl-5-carbethoxyamino phenol, 2-methoxy-5-carbethoxyamino phenol;

(f) metadiphenols such as resorcin and orcin;

(g) heterocyclic couplers such as 6-hydroxy benzomorpholine, 2,6-diaminopyridine, 3-methyl pyrazolone, 1,3-dimethyl pyrazolone, 1-phenyl-3-methyl pyrazolone.

The dyeing compositions according to the invention may also contain, in addition to the oxidation bases and couplers already mentioned, other products such as those hereinafter indicated taken singly or in combination:

1. The leucoderivatives of indoanilines and indophenols such as 4,4'-dihydroxy-2-amino-5-methyl diphenylamine, 4,4'-dihydroxy-2-amino-N-hydroxyethyl-5-methyl-2'-chloro diphenylamine, 2,4'-diamino-4-hydroxy-5-methyl diphenylamine;

2. The polyaminophenols, the monoaminodiphenols, the diaminodiphenols, the polyphenols such as trihydroxybenzene;

3. Direct dyes on the condition that they are resistant to hydrogen peroxide in an ammoniacal medium and, in particular, direct dyes of the benzene series such as 1-amino-N,N-dihydroxyethyl-3-nitro-4-amino-N'-methyl benzene; 1-amino-N,N-methyl-β-hydroxyethyl-3-nitro-4-amino-N'-β-hydroxyethyl benzene, 1-amino-N,N-methyl-β-hydroxyethyl-3-nitro-4-amino-N'-methyl benzene, 3-nitro-4-amino-N-β-hydroxyethyl anisole, 3-nitro-4-N-amino-β-hydroxyethyl phenol, (3-nitro-4-amino) phenoxyethanol, (3-nitro-4-amino-N-methyl) phenoxyethanol, 2-β-hydroxyethylamino-5-nitro anisole, 2-nitro-5-amino phenol and 2-nitro-5-amino-N-β-hydroxyethyl phenol.

4. Various usual additives such as penetrating agents, foaming agents, thickening agents, anti-oxidizing agents, alkalizing agents, perfumes, sequestrating agents, and film forming products.

The pH of the dyeing compositions according to the invention is a basic pH, for example, comprised between 8 and 11.5. One prefers a pH comprised between 9 and 10. Among the alkalizing agents which may be used, one may mention ammonia, the alkyl amines such as ethyl amine or triethyl amine, the alkanoamines such as the mono, di, or tri-ethanolamine, the ammonium derivatives, hydroxides of sodium or potassium, the carbonates of sodium or potassium.

One may also add to the composition according to the invention hydrosoluble anionic, cationic, non-ionic, or amphoteric surface-active agents. Among the surface-active agents particularly usable, one may mention the alkylbenzene-sulfates, the alkylnaphthalene-sulfonates, the sulfates, ethersulfates and sulfonates of fatty alcohols, the quaternary ammonium salts such as triethyl-cetylammonium bromide, cetylpyridinium bromide, the diethanolamides of fatty acids, the polyoxyethylenated acids and alcohols, and the polyoxyethylenated alkylphenols. Preferably the surface-active agents are present in the composition according to the invention in a proportion comprised between 0.5 and 30% by weight and preferably between 4 and 25% by weight.

One may also add to the composition according to the invention organic solvents to solubilize the compounds which are not sufficiently soluble in water. Among the solvents which one may advantageously use, one may mention by way of example, ethanol, isopropanol, glycerin, the glycols such as butyl-glycol, ethylene-glycol, propylene-glycol, monoethylether and monomethylether of diethylene-glycol, and analogous products. The solvents may be advantageously present in the composition in a proportion going from 1 to 40% by weight and preferably between 5 and 30% by weight.

The thickening products which may be added to the composition according to the invention may advantageously be taken in the group formed by sodium alginate, gum arabic, the derivatives of cellulose such as methylcellulose, hydroxy ethylcellulose, hydroxypropyl-methylcellulose, the sodium salt of carboxymethylcellulose and the polymers of acrylic acid. One may also use mineral thickening agents such as bentonite. Preferably the thickening agents are present in a proportion comprised between 0.5 and 5% by weight in proportion to the total composition preferably between 0.5 and 3% by weight.

The anti-oxidizing agents which one may add to the composition according to the invention may be taken in the group formed by sodium sulfite, thioglycolic acid, acid sodium sulfite, ascorbic acid, and hydroquinone. These anti-oxidizing agents may be present in the composition in a proportion comprised between 0.05 and 1% by weight in proportion to the total weight of the composition.

The dyeing composition according to the invention may contain oxidizing agents such as hydrogen peroxide, urea peroxide, or persalts such as the persulfate of ammonium.

In a general way, the compounds of formula (I) are present in the dyeing composition according to the invention in a proportion between 0.01% and 2% by weight in proportion to the total weight of the composition.

The dyeing composition according to the invention may be in the form of a liquid solution, a paste, a cream, a gel, or any other form appropriate for dyeing keratinic fibers.

In order that the object of the invention may be better understood, one will now describe by way of purely illustrative and non-limiting examples, the preparation of two compounds of formula (I) and the use of these compounds in dyeing compositions according to the invention:

EXAMPLE 1

Preparation of 2-methyl-5-amino-N-mesylaminoethyl phenol

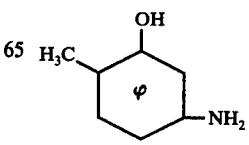 ⟶

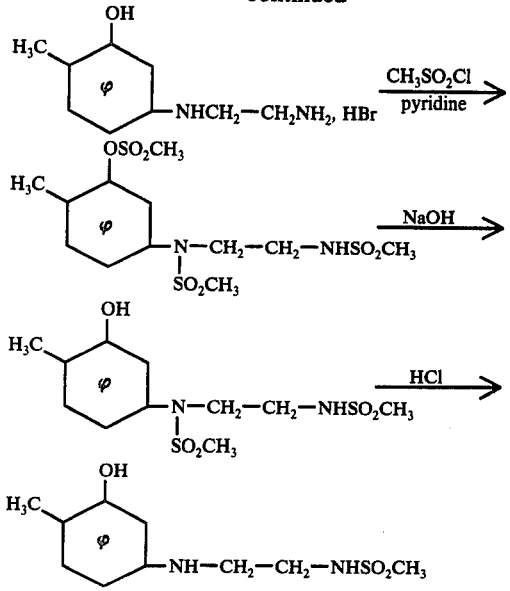

First step: Preparation of monohydrobromide of 2-methyl-5-β-aminoethylamino phenol.

One introduces into a flask 100 ml of water, 27 g of calcium carbonate and 0.5 mol (62 g) of 2-methyl-5-amino phenol. To this mixture, first brought to 95° C, one adds little by little, under agitation, 0.54 mol (112 g) of hydrobromide of bromoethylamine in 60 ml of water. The addition terminated, one maintains the heating and agitation for 20 minutes then one filters the hot reaction medium. After cooling, the monohydrobromide of 2-methyl-5-β-aminoethylamino phenol crystallizes. The product is drained, washed with a little acetone, and vacuum dried.

Second step: Preparation of 2-methyl-5-amino-N-mesyl-N-β-mesylaminoethyl mesyloxybenzene.

One dissolves 0.08 mol (20 g) of monohydrobromide of 2-methyl-5-β-aminoethylamino phenol in 60 ml of pyridine. To this solution maintained between 15 and 20° C one adds, little by little, under agitation, 0.30 mol (24 ml) of methanesulfochloride, then one maintains the reaction mixture for 2 hours at 20° C. It is then poured into 200 ml of iced 2.5 N hydrochloric acid. The expected product precipitates in the form of a gum which crystallizes rapidly. The product is drained, washed with water and dried. It melts at 135° C.

Third step: Preparation of 2-methyl-5-amino-N-mesyl-N-β-mesylamino-ethyl phenol.

One introduces 0.07 mol (28 g) of 2-methyl-5-amino-N-mesyl-N-β-mesylaminoethyl mesyloxybenzene into 60 ml of a 4 N soda solution. The reaction medium is heated for 3 hours in a boiling water bath. After cooling, it is neutralized with acetic acid. The expected product precipitates in the form of a gum which crystallizes slowly. The product is drained, washed in water, and recrystallized in water. After vacuum drying it melts at 130° C.

The results of the analysis are as follows:

| Analysis | Calculated for $C_{11}H_{18}N_2O_5S_2$ | Found |
| --- | --- | --- |
| C % | 40.98 | 41.05 |
| H % | 5.63 | 5.47 |
| N % | 8.69 | 8.88 |
| S % | 19.89 | 19.70 |

Fourth step: Preparation of 2-methyl-5-mesylaminoethylamino phenol.

One introduces 0.062 mol (20 g) of 2-methyl-5-amino-N-mesyl-N-β-mesylaminoethyl phenol in 20 ml of hydrochloric acid (density d = 1.19) and heats the reaction mixture for 16 hours at 110° C. It is then cooled, 20 ml of water is added, and the hydrochloric solution is neutralized with ammonia. The expected product precipitates in crystallized form. It is washed with water, recrystallized in ethanol and vacuum dried. It melts at 145° C.

The results of the analysis are the following:

| Analysis | Calculated for $C_{10}H_{16}N_2O_3S$ | Found |
| --- | --- | --- |
| C % | 49.17 | 48.97 |
| H % | 6.60 | 6.67 |
| N % | 11.47 | 11.60 |
| S % | 13.10 | 13.33 |

EXAMPLE 2

Preparation of 2-methyl-5-amino-N-mesyl, N-methylaminoethyl phenol:

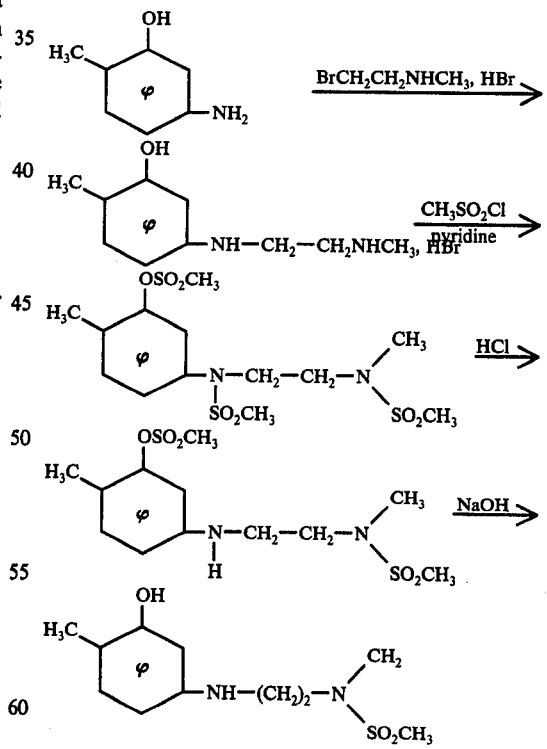

First step: Preparation of monobromohydride of 2-methyl-5-amino-N-β-methylaminoethyl phenol.

One introduces into a flask 0.1 mol (12.3 g) of 2-methyl-5-amino phenol, 35 ml of water, 8 ml of isopropanol and 6 g of calcium carbonate. Into this mixture, first brought to 95° C, one adds little by little, under agitation, 0.13 mol (29 g) of hydrobromide of N-bromoethyl-N-methylamine in 16 ml of water. The addition being terminated, one maintains the heating for 30 minutes, then one filters the reaction medium. After cooling the monohydrobromide of the expected product crystallizes. The product is drained, washed in acetone and vacuum dried.

The results of analysis are the following:

| | |
|---|---|
| Molecular weight calculated for $C_{10}H_{16}N_2O$, HBr | = 261 |
| Molecular weight found by potentiometric analysis in acetic acid with perchloric acid | = 262 |

Second step: Preparation of 2-methyl-N-mesyl,N-β-mesyl, 5-methylaminoethylamino mesyloxybenzene.

One dissolves 0.05 mol (13 g) of monohydrobromide of 2-methyl-5-amino-β-N-methylaminoethyl phenol in 45 ml of pyridine. In this solution maintained between 30° and 40° C one adds little by little, under agitation, 0.185 mol (15 ml) of methanesulfochloride. One leaves the reaction mixture overnight at the ambient temperature, then one pours it into 150 ml of 2.5 N hydrochloric solution. The expected product precipitates in crystallized form. It is drained, washed with water, recrystallized in ethanol. After vacuum drying, it melts at 168° C.

The results of the analysis are the following:

| Analysis | Calculated for $C_{13}H_{22}N_2O_7S_3$ | Found |
|---|---|---|
| S % | 23.21 | 22.97 |

Third step: Preparation of 2-methyl,N-β-mesyl-5-methylaminoethylamino mesyloxybenzene.

One heats to reflux for 27 hours 0.0385 mol (16 g) of the compound prepared during the above second step in 40 ml of hydrochloric acid (density d = 1.19) to which 40 ml of acetic acid is added. After cooling it is filtered to eliminate a light insoluble. One adds 100 ml of water, neutralizes with the aid of ammonia. The expected product precipitates. It is drained, washed with water, recrystallized in methanol. It melts at 102° C.

The results of the analysis are as follows:

| Analysis | Calculated for $C_{12}H_{20}N_2O_5S_2$ | Found |
|---|---|---|
| C % | 42.84 | 42.80 |
| H % | 5.99 | 5.91 |
| N % | 8.32 | 8.15 |
| S | 19.06 | 18.87 |

Fourth step: Preparation of 2-methyl-N-β-mesyl, 5-methylaminoethylamino phenol.

One introduces 0.0327 mol (11 g) of the foregoing compound obtained during the third of the above steps in 25 ml of a 4N soda solution. It is heated for 3 hours in a boiling water bath. After cooling and the elimination of a light insoluble by filtration, the soda solution is neutralized with acetic acid. The expected product precipitates. It is washed with water, recrystallized in methanol and vacuum dried. It melts at 122° C.

| Analysis | Calculated for $C_{11}H_{18}O_3N_2S$ | Found |
|---|---|---|
| C % | 51.15 | 51.18 |
| H % | 7.03 | 6.96 |
| N % | 10.85 | 10.70 |
| S % | 12.39 | 12.56 |

EXAMPLE 3

The following dyeing composition is prepared:

| | | |
|---|---|---|
| Compound of example 1 | | 0.015 g |
| Dihydrochloride of 4-N-methylamino aniline | | 0.012 g |
| Monomethyl ester of diethylene-glycol | | 10 g |
| Ammonia at 22° B q.s. | pH = | 10.3 |
| Water, q.s. | 100 | g |

At the moment of use one adds 25 g of hydrogen peroxide at 20 volumes.

This mixture applied to bleached hair for 30 minutes at ambient temperature imparts thereto, after rinsing and shampooing, a clear raw silk color tinted with mauve.

EXAMPLE 4

The following dyeing composition is prepared:

| | |
|---|---|
| Compound of example 1 | 0.814 g |
| Dihydrochloride of 4-amino-N-methyl aniline | 0.65 g |
| Butylglycol | 10 g |
| Ammonia at 22° B | 10 g |
| Water, q.s. | 100 g |

The pH is equal to 9.8. At the moment of use 100 g of hydrogen peroxide at 20 volumes is added.

This mixture applied to bleached hair for 30 minutes at 25° C imparts thereto, after rinsing and shampooing, a very sombre strong violet coloration.

EXAMPLE 5

The following dyeing composition is prepared:

| | |
|---|---|
| Composition of example 1 | 0.610 g |
| Dihydrochloride of paraphenylenediamine | 0.452 g |
| Sodium lauryl sulfate with 19% of the starting oxyethylenated alcohol | 20 g |
| Product known under the trade name "Trilon B" | 0.2 g |
| Sodium bisulfite at 40% | 1 g |
| Ammonia at 22° B | 10 g |
| Water, q.s. | 100 g |

The pH is equal to 10.2. At the moment of use, 100 g of hydrogen peroxide at 20 volumes is added.

This mixture applied for 20 minutes at 25° C to 95% naturally white hair imparts thereto, after rinsing and shampooing, a sombre purple red coloration.

EXAMPLE 6

The following dyeing composition is prepared:

| | |
|---|---|
| Composition of example 2 | 0.645 g |
| Paraaminophenol | 0.272 g |
| Sodium lauryl sulfate with 19% of the starting oxyethylenated alcohol | 20 g |
| Product sold under the commercial name "Trilon B". | 0.2 g |
| Sodium bisulfite at 40% | 1 g |
| Ammonia at 22° B | 10 g |
| Water, q.s. | 100 g |

The pH is equal to 10.4. At the moment of use 100 g of hydrogen peroxide at 20 volumes is added.

This mixture applied for 20 minutes at 30° C to bleached hair imparts thereto, after rinsing and shampooing, an golden apricot color.

EXAMPLE 7

The following dyeing composition is prepared:

| | |
|---|---|
| Compound of example 2 | 0.8 g |
| Dihydrochloride of 4-amino-N-β-methoxyethyl aniline | 0.74 g |
| Diethanolamides of fatty acids of copra | 10 g |
| Triethanolamine, q.s.      pH = | 8.1 |
| Water, q.s. | 100 g |

At the moment of use, one adds 100 g of hydrogen peroxide at 20 volumes.

This mixture applied for 25 minutes at 25° C to bleached hair imparts thereto, after rinsing and shampooing, a sombre purple violet coloration.

EXAMPLE 8

The following dyeing composition is prepared:

| | |
|---|---|
| Compound of example 1 | 1.22 g |
| 4-amino-N-ethyl, N-mesylaminoethyl-2-methyl aniline | 1.355 g |
| Butylglycol | 10 g |
| Product sold under the commercial name "Carbopol 934" (polymer of acrylic acid M.W. = 2 at 3 millions) manufactured by the Goodrich Chemical Company | 4.5 g |
| Ammonia at 22° B, q.s.     pH = | 8.8 |
| Water, q.s. | 100 g |

At the moment of use, 60 g of hydrogen peroxide at 20 volumes is added.

This mixture applied for 5 minutes at ambient temperature to bleached hair imparts thereto, after rinsing and shampooing, a silver blue coloration.

EXAMPLE 9

The following dyeing composition is prepared:

| | |
|---|---|
| Compound of example 2 | 1.0 g |
| 4-amino-N-ethyl,N-mesylaminoethyl-2-methyl aniline | 1.05 g |
| Oleic alcohol oxyethylenated with 2 mols of ethylene oxide | 5 g |
| Oleic alcohol oxyethylenated with 4 mols of ethylene oxide | 10 g |
| Propyleneglycol | 10 g |
| Ammonia at 22° B    q.s.    pH = | 10 |
| Water, q.s. | 100 g |

At the moment of use, one adds 100 g of hydrogen peroxide at 20 volumes.

This mixture applied for 20 minutes at 20° C to bleached hair imparts thereto, after rinsing and shampooing a very bright slightly voilet blue.

EXAMPLE 10

The following dyeing composition is prepared:

| | |
|---|---|
| Compound of example 1 | 1.8 g |
| 4-amino-N,N-di-β-hydroxyethyl aniline sulfate | 2.175 g |
| Butylglycol | 15 g |
| Alcohol at 96° | 35 g |
| Ammonia at 22° B | 5 g |
| Water, q.s. | 100 g |

The final pH is equal to 9.6. At the moment of use, 90 g of hydrogen peroxide at 20 volumes is added.

This mixture applied for 10 minutes at ambient temperature, to bleached hair, imparts thereto, after rinsing and shampooing, a very bright silver mauve coloration.

EXAMPLE 11

The following dyeing composition is prepared:

| | |
|---|---|
| Compound of example 1 | 0.38 g |
| Dihydrochloride of (2,4-diamino) phenoxyethanol | 0.055 g |
| Dihydrochloride of 4-amino-N-γ-methoxypropyl aniline | 0.41 g |
| 3-nitro-4-amino-N-β-hydroxyethyl phenol | 0.20 g |
| 2-nitro-5-amino phenol | 0.195 g |
| Oleic alcohol oxyethylenated at 2 mols of ethylene oxide | 4.5 g |
| Oleic alcohol oxyethylenated with 4 mols of ethylene oxide | 9 g |
| Propyleneglycol | 10 g |
| Ammonia at 22° B | 10 g |
| Water, q.s. | 100 g |

The pH is equal to 10.5. At the moment of use, 100 g of hydrogen peroxide at 20 volumes is added.

This mixture applied for 20 minutes at ambient temperature to bleached hair imparts thereto, after rinsing and shampooing, a metallic grey coloration.

EXAMPLE 12

| | |
|---|---|
| Compound of example 1 | 0.35 g |
| 4-amino-N,N-di-β-hydroxyethyl aniline sulfate | 0.156 g |
| Hydrochloride of 2-methyl-4-amino phenol | 0.20 g |
| 2-nitro-5-β-hydroxyethylamino phenol | 0.30 g |
| Propyleneglycol | 15 g |
| Carboxymethylcellulose | 4 g |
| Ammonia at 22° B | 5 g |
| Water, q.s. | 100 g |

The pH is equal to 10.7. At the moment of use, 100 g of hydrogen peroxide at 20 volumes is added.

This mixture applied for 20 minutes at ambient temperature to 95% white hair imparts thereto, after rinsing and shampooing, a deep golden blonde coloration.

EXAMPLE 13

The following dyeing composition is prepared:

| | |
|---|---|
| Compound of example 1 | 0.208 g |
| 4-amino-N,N-di-β-hydroxyethyl aniline sulfate | 0.125 g |
| Hydrochloride of 2-methyl-4-amino phenol | 0.083 g |
| 2-nitro-5-amino-N-β-hydroxyethyl phenol | 0.25 g |
| Propyleneglycol | 12.5 g |
| Carboxymethylcellulose | 4 g |
| Ammonia at 22° B | 8.5 g |
| Water, q.s. | 100 g |

The final pH is equal to 10.5. At the moment of use, 100 g of hydrogen peroxide at 20 volumes is added.

This mixture applied for 25 minutes at ambient temperature to bleached hair imparts thereto, after rinsing and shampooing, a clear slightly burnt blonde coloration.

EXAMPLE 14

The following dyeing composition is prepared:

| | |
|---|---|
| Composition of example 1 | 0.22 g |
| Dihydrochloride of 4-amino-N-methyl aniline | 0.2 g |
| 2-β-hydroxyethylamino-5-nitro anisole | 0.21 g |
| 2,4'-diamino-4-hydroxy-5-methyl diphenylamine | 0.16 g |
| Butylglycol | 15 g |
| Product known under the commercial "Carbopol 934" (polymer of acrylic acid M.W=2 to 3 millions) | |

| | | |
|---|---|---|
| -continued | | |
| manufactured by the Goodrich Chemical Co. | 3.46 | g |
| Ammonia at 22° B | 8 | g |
| Water, q.s. | 100 | g |

The pH is equal to 9.1. At the moment of use, 70 g of hydrogen peroxide at 20 volumes is added.

This mixture applied for 20 minutes at 25° C to bleached hair imparts thereto, after rinsing and shampooing, a deep chestnut coloration having red copper glints.

EXAMPLE 15

The following dyeing composition is prepared:

| | | |
|---|---|---|
| Dihydrochloride of 2,6-dimethyl-3-methoxy para-phenylenediamine | 0.61 | g |
| Compound of example 1 | 0.35 | g |
| 2-methyl-5-ureido phenol | 0.265 | g |
| Hydrochloride of 3-chloro-4-amino phenol | 0.25 | g |
| (3-nitro-4-amino) phenoxyethanol | 0.10 | g |
| Alcohol at 96° | 10 | g |
| Nonylphenol having 4 mols of ethylene oxide | 17 | g |
| Nonylphenol having 9 mols of ethylene oxide | 17 | g |
| Ammonia at 22° B | 5 | g |
| Water, q.s. | 100 | g |

The pH is equal to 9.9. At the moment of use, 100 g of hydrogen peroxide at 20 volumes is added.

This mixture applied for 20 minutes at ambient temperature to bleached hair imparts thereto, after rinsing and shampooing, a rosy beige coloration.

EXAMPLE 16

The following dyeing composition is prepared:

| | | |
|---|---|---|
| Compound of example 1 | 0.30 | g |
| Paraaminophenol | 0.23 | g |
| 4-amino-N,N-dihydroxyethyl aniline sulfate | 0.20 | g |
| 6-hydroxy benzomorpholine | 0.165 | g |
| 3-nitro-3-N-β-hydroxyethylamino aniline | 0.10 | g |
| Butylglycol | 15 | g |
| Diethanolamides of fatty acids of copra | 8.2 | g |
| Ammonia at 22° B | 3 | g |
| Water, q.s. | 100 | g |

The pH is equal to 9.8. At the moment of use, 70 g of hydrogen peroxide at 20 volumes is added.

This mixture applied for 15 minutes at ambient temperature to bleached hair imparts thereto, after rinsing and shampooing, a clear mahogany coloration.

EXAMPLE 17

The following dyeing composition is prepared:

| | | |
|---|---|---|
| Compound of example 1 | 0.41 | g |
| Resorcine | 0.42 | g |
| Dihydrochloride of (2,4-diamino) phenoxyethanol | 0.40 | g |
| Dihydrochloride of paraphenylenediamine | 1.4 | g |
| 4-amino-N-ethyl-N-carbamylmethyl aniline | 0.30 | g |
| Paraaminophenol | 0.70 | g |
| Sodium lauryl sulfate with 19% of the starting oxyethylenated alcohol | 20 | g |
| Product sold under the commercial name "Trilon B" | 0.2 | g |
| Sodium bisulfite at 40% | 1 | g |
| Ammonia at 22° B | 10 | g |
| Water, q.s. | 100 | g |

The pH is 9.7. At the moment of use 100 grams of hydrogen peroxide at 20 volumes are added.

This mixture applied for 20 minutes at 25° C to bleached hair imparts thereto, after rinsing and shampooing, a blackish brown coloration having violet glints.

EXAMPLE 18

The following dyeing composition is prepared:

| | | |
|---|---|---|
| Compound of example 1 | 0.25 | g |
| Dihydrochloride of 4-amino-N-γ-methoxypropyl benzene | 0.60 | g |
| 2-amino-N-carbamylmethyl-4-amino anisole | 0.10 | g |
| 1-phenyl methylpyrazolone | 0.10 | g |
| 4,4'-dihydroxy-2-amino-5-methyl diphenylamine | 0.62 | g |
| 3-nitro-4-amino-N-β-hydroxyethyl phenol | 0.08 | g |
| Dihydrochloride of 2,6-diamino hydroquinone | 0.25 | g |
| Butylglycol | 10 | g |
| Carboxymethylcellulose | 4.2 | g |
| Ammonia at 22° B | 6 | g |
| Water, q.s. | 100 | g |

The pH is equal to 10.2. At the moment of use, 90 g of hydrogen peroxide is added.

This mixture applied for 20 minutes at ambient temperature to bleached hair imparts thereto, after rinsing and shampooing, a deep coppery red chestnut coloration.

EXAMPLE 19

The following dyeing composition is prepared:

| | | |
|---|---|---|
| Compound of example 1 | 0.32 | g |
| Compound of example 2 | 0.21 | g |
| Dihydrochloride of 2,6-dimethyl paraphenylenediamine | 0.45 | g |
| Hydrochloride of 3-chloro-4-amino phenol | 0.35 | g |
| Dihydrochloride of 2,6-diamino-4-amino N,N-diethyl phenol | 0.25 | g |
| Dihydrochloride of 2,6-diamino hydroquinone | 0.05 | g |
| Ammonium alkyl sulfate in $C_{12}$-$C_{14}$ (70% of $C_{12}$, 30% of $C_{14}$) | 15 | g |
| Lauric alcohol having 10.5 mols of ethylene oxide | 5 | g |
| Ammonia at 22° B | 15 | g |
| Water, q.s. | 100 | g |

The final pH is equal to 10.2. At the moment of use 75 g of hydrogen peroxide at 20 volumes is added.

The mixture applied for 20 minutes at ambient temperature to bleached hair imparts thereto, after rinsing and shampooing, a rosy golden blonde coloration.

EXAMPLE 20

The following dyeing composition is prepared:

| | | |
|---|---|---|
| Compound of example 1 | 0.5 | g |
| Metaaminophenol | 0.2 | g |
| 2,6-dimethyl-5-acetylamino phenol | 0.1 | g |
| Paraaminophenol | 0.5 | g |
| 4-amino-N-methyl phenol sulfate | 0.6 | g |
| 4-amino-N-β-methoxyethyl aniline sulfate | 1 | g |
| Butylglycol | 5 | g |
| Nonylphenol having 4 mols of ethylene oxide | 17 | g |
| Nonylphenol having 9 mols of ethylene oxide | 17 | g |
| Ammonia at 22° B | 10 | g |
| Water, q.s. | 100 | g |

The pH is equal to 9.8. At the moment of use 85 g of hydrogen peroxide at 20 volumes is added.

This mixture applied for 20 minutes at ambient temperature to bleached hair imparts thereto, after rinsing and shampooing a hazel coloration.

EXAMPLE 21

The following dyeing composition is prepared:

| | |
|---|---|
| Compound of example 1 | 0.2 g |
| Paraaminophenol | 0.09 g |
| 6-hydroxy benzomorpholine | 0.03 g |
| Dihydrochloride of 4-N-β-methoxyethylamino aniline | 0.15 g |
| Butylglycol | 10 g |
| Nonylphenol having 4 mols of ethylene oxide | 20 g |
| Nonylphenol having 9 mols of ethylene oxide | 20 g |
| Ammonia at 22° B | 5 g |
| Water, q.s. | 100 g |

The pH is equal to 10. At the moment of use, 50 g of hydrogen peroxide at 20 volumes is added.

This mixture applied for 25 minutes at 25° C to bleached hair imparts thereto, after rinsing and shampooing, a very clear nacreous rosy blonde coloration.

EXAMPLE 22

The following dyeing composition is prepared:

| | |
|---|---|
| Compound of example 1 | 0.05 g |
| 2,6-dimethyl-5-acetylamino phenol | 0.20 g |
| Dihydrochloride of 4-amino-N-β-methoxyethyl aniline | 0.30 g |
| Paraaminophenol | 0.03 g |
| Ammonium alkyl sulfate in C$_{12}$-C$_{14}$ (70% of C$_{12}$, 30% of C$_{14}$) | 15 g |
| Lauric alcohol having 10.5 mols of ethylene oxide | 5 g |
| Ammonia at 22° B | 10 g |
| Water, q.s. | 100 g |

The pH is equal to 9.9. At the moment of use 100 g of hydrogen peroxide at 20 volumes is added.

This mixture applied for 20 minutes at ambient temperature to 90% naturally white hair imparts thereto, after rinsing and shampooing, a bluish silver grey.

We claim:

1. A dyeing composition for keratinic fibers or for human hair, containing an aqueous solution of at least one oxidation base which contains as a coupler, at least one compound of the formula

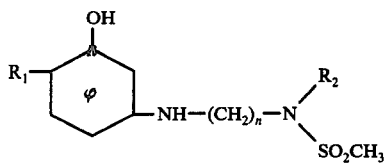

(I)

in which $R_1$ represents an alkyl having 1 to 4 carbon atoms, $R_2$ represents hydrogen or an alkyl having 1 to 4 carbon atoms, and $n$ is a number having a value of 2 or 3.

2. The composition of claim 1 which contains as an oxidation base at least one paraphenylenediamine of the general formula

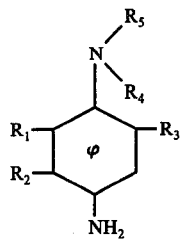

(II)

or a corresponding acid salt, in which $R_1$, $R_2$ and $R_3$ are identical or different and represent hydrogen, alkyl having 1 to 2 carbon atoms, or alkoxy having 1 to 2 carbon atoms, $R_4$ and $R_5$ are identical or different and represent hydrogen, alkyl, hydroxyalkyl, alkoxyalkyl, in which the alkoxy group comprises 1 to 2 carbon atoms, carbamylalkyl, mesylaminoalkyl, acetylaminoalkyl, ureidoaminoalkyl, carbethoxyaminoalkyl, the alkyl groups in $R_4$ and $R_5$ having 1 to 3 carbon atoms with the reservation that $R_1$ or $R_3$ represents hydrogen when $R_4$ and $R_5$ do not represent hydrogen.

3. The composition of claim 2 which contains at least one paraphenylenediamine of formula (II) selected from the group consisting of paraphenylenediamine, 2,6-dimethyl paraphenylenediamine, 2,6-dimethyl-5-methoxy paraphenylenediamine, 4-amino-N-methyl aniline, 4-amino-N-methoxyethyl aniline, 4-amino-N,N-di-hydroxyethyl aniline, 4-amino-N-ethyl-N-carbamylmethyl aniline and 4-amino-N-ethyl-N-mesylaminoethyl aniline.

4. The composition of claim 1 which contains as an oxidation base, at least one paraaminophenol.

5. The composition of claim 4 which contains at least one paraaminophenol selected from the group consisting of paraaminophenol, 2-methyl-4-amino phenol and 3-chloro-4-amino phenol.

6. The composition of claim 1, which contains in addition to the coupler or couplers of formula (I), at least one coupler selected from the group consisting of:
(a) metaphenylenediamines such for example, as 2,4-diamino anisole, 2,4-diamino phenoxyethanol, (2-amino-4-amino-N-methyl) phenoxyethanol, (2,4-diamino) phenyl-β-methoxyethylether, 2-carbamylmethylamino-4-amino anisole,
(b) metaaminophenols such as metaaminophenol, 2-methyl-5-amino phenol, 2-methyl-5-amino-N-β-hydroxyethyl phenol, 2-methyl-5-carbamylmethylamino phenol, 2,6-dimethyl-5-amino phenol,
(c) metaacetylaminophenols such as 2-methyl-5-acetylamino phenol, 2-6-dimethyl-5-acetylamino phenol, 2-methoxy-5-acetylamino phenol,
(d) metaureidophenols such as 2-methyl-5-ureido phenol,
(e) metacarbethoxyphenols such as 2-methyl-5-carbethoxyamino phenol, 2-methoxy-5-carbethoxyamino phenol,
(f) metadiphenols such as resorcin and orcin,
(g) heterocyclic couplers such as 6-hydroxy benzomorpholine, 2,6-diaminopyridine, 3-methyl pyrazolone, 1,3-dimethyl pyrazolone, 1-phenyl-3-methyl pyrazolone.

7. The composition of claim 1, which contains, in addition to the oxidation bases and couplers, at least one dyeing product selected from the group consisting of:
(a) the leucoderivatives of indoanilines and indophenols,
(b) polyaminophenols, monoaminodiphenols, diaminodiphenols and polyphenols,
(c) direct dyes or the nitrated dyes of the benzene series.

8. The composition of claim 1 which contains at least one additive selected from the group consisting of penetrating agents, foaming agents, thickening agents, antioxidating agents, alkalizing agents, perfumes, sequestrating agents and film forming products.

9. The composition of claim 1 which contains 0.01 to 2% by weight of at least one compound of formula (I) in proportion to the total weight of the composition.

10. The composition of claim 1 which has a pH between 8 and 11.5.

11. The composition of claim 10 wherein said pH is between 9 and 10.

* * * * *